United States Patent
Peng et al.

(10) Patent No.: US 12,020,453 B2
(45) Date of Patent: Jun. 25, 2024

(54) FAST VOLUMETRIC IMAGING SYSTEM AND PROCESS FOR FLUORESCENT TISSUE STRUCTURES AND ACTIVITIES

(71) Applicant: Arizona Board of Regents on Behalf of the University of Arizona, Tucson, AZ (US)

(72) Inventors: Leilei Peng, Tucson, AZ (US); Jun Ding, Palo Alto, CA (US); Dongli Xu, Palo Alto, CA (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 344 days.

(21) Appl. No.: 17/426,803

(22) PCT Filed: Jan. 29, 2020

(86) PCT No.: PCT/US2020/015676
§ 371 (c)(1),
(2) Date: Jul. 29, 2021

(87) PCT Pub. No.: WO2020/160146
PCT Pub. Date: Aug. 6, 2020

(65) Prior Publication Data
US 2022/0122284 A1    Apr. 21, 2022

Related U.S. Application Data

(60) Provisional application No. 62/798,146, filed on Jan. 29, 2019.

(51) Int. Cl.
*G06T 7/73*    (2017.01)
*G01N 21/64*    (2006.01)
(Continued)

(52) U.S. Cl.
CPC ........... *G06T 7/73* (2017.01); *G01N 21/6402* (2013.01); *G01N 21/6428* (2013.01);
(Continued)

(58) Field of Classification Search
CPC .. H04N 1/195; H04N 1/19594; H04N 1/3876; H04N 19/54; H04N 2201/0414;
(Continued)

(56) References Cited

U.S. PATENT DOCUMENTS

| | | | | |
|---|---|---|---|---|
| 2010/0178650 A1* | 7/2010 | Karsten | ................ | G02B 21/06 |
| | | | | 359/398 |
| 2011/0081653 A1* | 4/2011 | Hell | ...................... | G02B 27/58 |
| | | | | 435/6.19 |

(Continued)

FOREIGN PATENT DOCUMENTS

| | | | | |
|---|---|---|---|---|
| DE | 102012224306 A1 * | 6/2014 | ......... | G01N 21/6458 |
| ES | 2749742 A1 * | 3/2020 | ......... | G01N 21/6458 |

(Continued)

OTHER PUBLICATIONS

International Search Report and Written Opinion for International Application No. PCT/US20/15676 dated Apr. 8, 2020; 8 pages.

*Primary Examiner* — Behrooz M Senfi
(74) *Attorney, Agent, or Firm* — Bond, Schoeneck & King, PLLC; George R. McGuire

(57) ABSTRACT

A microscopic technique for generating high-clarity, large volume 3D images of fluorescent tissue structure at subcellular resolution and capture transient activities. The technique includes capturing two orthogonal 2D projection of the sample volume by performing a projection scan with an excitation laser sweeping through the volume at up to 100 vps, tracking the scan depth using an electrically tuned lens to keep the emission image in focus and generate an xy plane volume projection image at the camera; and placing a PMT (Continued)

behind the excitation lens to collect emission passed through the excitation lens, wherein signals from the PMT form a focus scan projection at the yz plane; and then merging the xy and yz projections.

9 Claims, 3 Drawing Sheets

(51) Int. Cl.
*G02B 21/00* (2006.01)
*G02B 21/36* (2006.01)
*G06T 7/11* (2017.01)
*G06T 7/62* (2017.01)
*H04N 23/67* (2023.01)

(52) U.S. Cl.
CPC ..... *G01N 21/6456* (2013.01); *G02B 21/0076* (2013.01); *G02B 21/365* (2013.01); *G06T 7/11* (2017.01); *G06T 7/62* (2017.01); *H04N 23/671* (2023.01); *G01N 2021/6441* (2013.01); *G01N 2201/06113* (2013.01); *G06T 2207/10056* (2013.01)

(58) Field of Classification Search
CPC ............... H04N 5/2624; H04N 23/671; G01N 2021/1785; G01N 2021/6441; G01N 21/6402; G01N 21/6428; G01N 21/6456; G01N 2201/06113; G06T 2207/10056; G06T 7/11; G06T 7/62; G06T 7/73; G02B 21/0036; G02B 21/0076; G02B 21/365
USPC .......................................................... 348/135
See application file for complete search history.

(56) References Cited

U.S. PATENT DOCUMENTS

| | | | |
|---|---|---|---|
| 2014/0355862 A1* | 12/2014 | So | ........................ G06V 20/69 382/133 |
| 2016/0139050 A1 | 5/2016 | Wuite et al. | |
| 2018/0042483 A1 | 2/2018 | Bardhan et al. | |

FOREIGN PATENT DOCUMENTS

| | | | | |
|---|---|---|---|---|
| JP | 2004177662 A | * | 6/2004 | ............. G02B 21/06 |
| WO | WO-2011105507 A1 | * | 9/2011 | ............. C12N 1/066 |

* cited by examiner

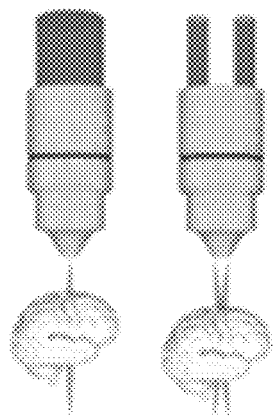 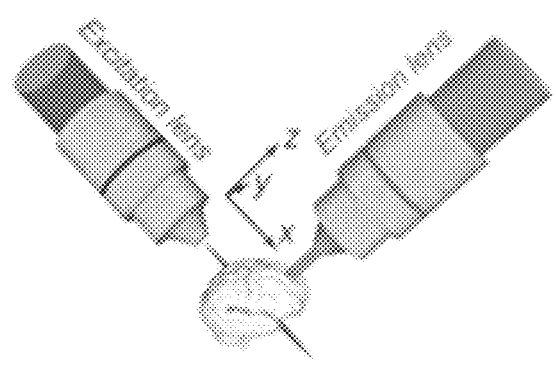
FIG. 1A   FIG. 1B   FIG. 1C

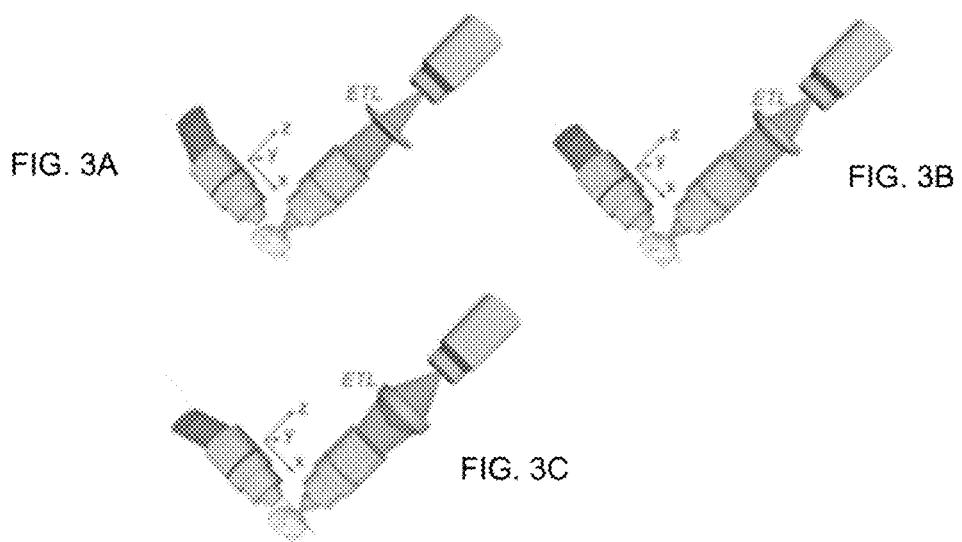

FAST VOLUMETRIC IMAGING SYSTEM AND PROCESS FOR FLUORESCENT TISSUE STRUCTURES AND ACTIVITIES

CROSS-REFERENCE TO RELATED APPLICATION

The present application is a National Stage Application, filed under 35 U.S.C. 371, of International Patent Application No. PCT/US20/15676, filed on Jan. 29, 2020, which relates and claims priority to U.S. Provisional Application No. 62/798,146, filed Jan. 29, 2019, the entire contents of each of which is hereby incorporated by reference.

GOVERNMENT FUNDING

N/A

FIELD OF THE INVENTION

The present disclosure is directed generally to fast volumetric imaging of fluorescent tissue structures and activities.

BACKGROUND

In order to study complex dynamics of tissue in live animals, ideally the microscope needs to maintain the submicron resolution in deep tissue to resolve activities in subcellular structures, cover a large volume to analyze complex networks, and refresh the volumetric image at high speed to capture transient dynamics. However, despite many processes, at present there are no known microscopic techniques that fully satisfy the need for resolution, penetration, volume and speed. Common existing techniques can be categorized in three categories:

One photon excitation microscopy, either by wide field imaging capture or point scanning. These techniques have high imaging speeds but can only maintain high resolution in a small superficial volume because visible light is strongly scattered in tissue. Some of the advanced techniques in this category, for example, Light-field 3D imaging, can cover a large volume at a high speed but are unable to resolve subcellular structures.

Two-photon (2p) scanning microscopy. This category contains some of the most used methods for deep tissue imaging. IR light for 2p excitation penetrates deeper in tissue, allowing large volume imaging. But the imaging speed of scanning microscopy is limited to about 8k line scans per second, or 30 fps at a 512-by-512 image size. Random-access scanners can scan preselected points at a faster frame rate; however, a selective-observation technique is less desirable than an unbiased imaging technique.

Full field 2p imaging techniques, for example temporal focusing and 2p light sheet imaging. These techniques can reach the video frame rate but are still too slow for 3D imaging. Again, targeted multi-plane imaging can offer faster but biased 3D observation.

At present, the Bessel focus scanning technique offers the fastest 2p un-biased volume imaging rate at 30 volume per second (vps). The technique uses an elongated 2p excitation focus in an upright microscope to scan across tissue (see, FIG. 1A). Compared to the traditional tight focus 2p scanning imaging, which generates a 2D image of a 1-μm-thick thin tissue slice, Bessel focus scanning generates the projection image of a thick volume at 30 fps. Post image-processing is used to assign signals in projection images onto a pre-measured 3D structure, resulting in a 30 vps functional observation. The technique makes volume imaging as fast as 2D imaging and has had great success in various tissues. Despite its success, the technique still has limitations.

First, the projection images lack intrinsic depth resolution, and the post imaging processing method that renders depth resolution is only valid on highly sparse structures. To achieve optical 3D resolution from projection images, a pair of stereoscopic views can be acquired simultaneously with two tilted Bessel beams focused through the same objective lens (see, FIG. 1B). However, because the angle of stereo view is highly constrained by the numerical aperture reserved for focusing each beam and the total numerical aperture available from the lens, the depth resolving accuracy (±1.6 μm) of the stereoscopic method is much worse than the optical resolution limit (±0.5 μm) of the instrument.

Second, there is little room to improve the speed of Bessel focus scanning and vTwINS. Both techniques rely on resonant galvo-scanners to build projection images. Thus, their speeds are constrained by the speed of 8k projection lines per second. Increasing the frame speed will require sacrificing the image size.

To address these limitations in imaging fast transient activities in 3D, it is an object of the invention to develop a novel 2p microscopic technique that will generate high-resolution large-volume 3D images of tissue at subcellular resolution and capture transient activities within the volume at 100 volume per second (vps).

The present process will be based on the two-lens light sheet imaging framework (see, FIG. 1C). Traditionally, in a two-lens light sheet instrument, a scanning excitation laser is focused onto the tissue, and generates emission in a confined plane or sheet, which is collected by an emission lens that is oriented perpendicular to the plane. Compared to traditional scanning 2p imaging, light sheet 2p imaging offers a faster frame rate and avoids photon damage outside of the plane of interest. But it is not free of limitations. In recent years, there are rapid technique developments in the light sheet imaging field to overcome common limitations.

First, the sheet-width, or field-of-view is often narrow due to the short focus length of the beam. Previous work from one of the inventors' labs and other groups had shown that by using a Bessel beam to illuminate the plane, the field of view of light sheet imaging can be greatly extended to beyond 500 μm.

Second, emission images often quickly degrade in deep layers, because visible light is more susceptible to scattering in the tissue. Multi-view techniques, which take images from all four sides of the sample, can improve the image quality in small tissue samples such as zebrafish and drosophila, but is unsuitable for large tissue samples. One of the inventor's labs had established a unique scattering removal method, which is based on nonlinear structured illumination (NSIM), to restore optical resolution in deep tissue 2p light sheet images and enable sub-cellular imaging in depths beyond 250 μm in live zebrafish.

Last, 3D imaging is achieved be shifting the plane along the depth and is significantly slower than 2D imaging. Rapid depth scanning methods such as SCRAP and electric tunable focusing have been implemented to speed up the depth tuning. With these techniques and increasingly advancing high-speed camera technology, the speed of light sheet imaging keeps improving. But these advancements do not change the fact that 3D imaging requires tens of layers of 2D images being taken in sequence and is tens of times slower than 2D imaging. Furthermore, in real applications, simply increasing the imaging speed will result in dimmer images with degraded signal to noise ratio (SNR). To acquire a 10-layer 3D image at 100 vps, 2D images would need to be acquired at 1000 fps with less than 1 ms exposure time in each frame. Such short exposure time is unlikely to be compatible with existing genetically coded sensors, unless there is a better way to harvest the emission.

SUMMARY

The present disclosure is directed to fast volumetric imaging of fluorescent tissue structures and activities.

According to an aspect is a method for fast volumetric imaging of fluorescent tissue structures and activities, comprising the steps of acquiring two orthogonal 2D projections of the sample volume, comprising performing a projection scan with an excitation laser sweeping through the volume at a predetermined rate; tracking the scan depth using a focus tuning device, to keep the emission image in focus and generate an xy plane volume projection image at the camera; and placing a photomultiplier tube (PMT) behind the excitation lens to collect emission passed through the excitation lens, wherein signals from the PMT form a focus scan projection at the yz plane; and merging the xy and yz projections.

According to an embodiment, the predetermined rate is up to 100 vps.

According to an embodiment, the focus tuning device is an electrically tunable lens (ETL).

According to an embodiment, the method further comprises the step of labeling cell structure tissue of the sample volume with a first fluorescent emitting marker.

According to an embodiment, the method further comprises the step of labeling cell function tissue of the sample volume with a second fluorescent emitting marker.

According to an embodiment, the method further comprises the step of tracing the structures seen in 2D projections.

According to an embodiment, the method further comprises the step of reconstructing the 3D structure map by pairing the xy projection of a trace with its yz projection; looping though all xy plane pixel defined by the xy trace and assigning a z-value according to the corresponding yz projection trace result; searching for pixels on the yz projection trace that have the same y value at a given xy pixel on the trace; assigning a xy pixel with a single match the z-value of the matched yz pixel; comparing potential z-values with previously assigned z-values of adjacent xy pixels and assigning the xy pixel to a z-value that is closest to adjacent pixels; and repeating (steps i.-v.) on all traces.

According to an embodiment, the method further comprises the step of looping through all pixels in the xy projection image and assigning pixels that have an observable intensity to the z-value of its nearest trace pixel.

According to an embodiment, the method further comprises the step of segmenting the structures seen in 2D projections.

According to an embodiment, the method further comprises the step of reconstructing the 3D structure map by pairing the xy projection of a segment with its yz projection; looping though all xy plane pixel defined by the xy segment and assigning a z-value according to the corresponding yz projection segment result; searching for pixels on the y-z projection segment that have the same y-value at a given x-y pixel on the segment; assigning a xy pixel with a single match the z-value of the matched yz pixel; comparing potential z-values with previously assigned z-values of adjacent xy pixels, and assigning the xy pixel to a z-value that is closest to adjacent pixels; and repeating (steps i.-v.) on all segments.

According to an embodiment, the method further comprises the step of looping through all pixels in the xy projection image and assigning pixels that have an observable intensity to the z-value of its nearest segment pixel.

According to an aspect is a system for fast volumetric imaging of fluorescent tissue structure and activities, comprising: first and second lenses each orthogonally positioned relative to the fluorescent tissue structure for acquiring two orthogonal 2D projections of the sample volume; an excitation laser for performing a projection scan by sweeping through the volume at a predetermined rate; a focus tuning device to track the scan depth and keep the emission image in focus and generate an xy plane volume projection image; and a photomultiplier tube positioned behind the first lens.

These and other aspects of the invention will be apparent from the embodiments described below.

BRIEF DESCRIPTION OF THE DRAWINGS

The present invention will be more fully understood and appreciated by reading the following Detailed Description in conjunction with the accompanying drawings, in which:

FIG. 1A is a prior art schematic view of a 2p volumetric imaging technique using Bessel focus scanning imaging.

FIG. 1B is a prior art schematic view of a 2p volumetric imaging technique using two tiled Bessel beams to scan tissue simultaneously.

FIG. 1C is a prior art schematic view of a 2p volumetric imaging technique using light sheet imaging.

FIGS. 3A-3C are sequential schematic representations of using ETL to electrically tune the focusing depth of the camera during a light sheet depth scan, in accordance with an embodiment.

DETAILED DESCRIPTION OF EMBODIMENTS

The present disclosure describes fast volumetric imaging of fluorescent tissue structures and activities.

Figure 2A:
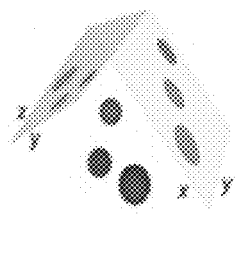
FIG. 2A is a conceptual rendering of using two orthogonal projection images to resolve to a 3D structure, in accordance with an embodiment.
Figure 2B:
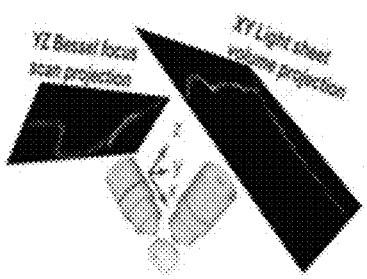
FIG. 2B is a schematic view of dual projection imaging in a two-objective light sheet setup, in accordance with an embodiment.

To speed up 3D imaging in a light sheet instrument, the present invention breaks away from the traditional plane-scanning approach and implements volumetric projection imaging instead. The two-lens framework provides the unique opportunity of acquiring two orthogonal 2D projection of the sample volume (see, FIG. 2A). During the projection scan, the excitation laser will sweep through the volume at up to 100 vps. An electrically tuned lens will track the scan depth, keep the emission image in focus (FIG. 3), and generate an xy plane volume projection image at the camera (FIG. 2B right). Meanwhile, a PMT will be placed behind the excitation lens to collect emission passed through the excitation lens. Signals from the PMT form a focus scan projection at the yz plane (FIG. 2B left).

Figure 2C:
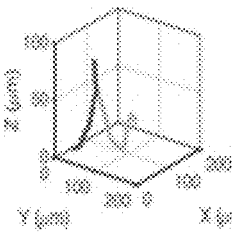
FIG. 2C is an image of 3D traced dendrites obtained from XY and YZ projections, in accordance with an embodiment.
Figure 2D:
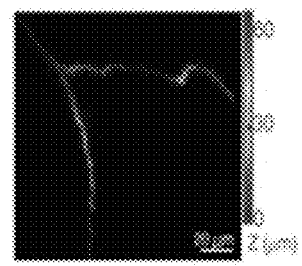
FIG. 2D is a 3D pseudo color rendering of the entire image volume, in accordance with an embodiment.

The technique combines Bessel focus scan with depth-tuned light sheet imaging. The combination gives the present method intrinsic 3D resolution. Compared to vTwINS, which generates two views at a small angle, two projections in the present method orientate in an ideal angle for 3D imaging. The resolution of the present method is expected to be the same as traditional 2p point scanning imaging. Unlike vTwINS, in which two views tangle together in a single image and require complex image processing, the present method generates two separate projection images that are easy to process. With simple 2D tracing and a MATLAB program to merge xy and yz traced paths, it is possible to produce 3D traces of the dendrite branch seen in the pair of projections (FIG. 2C). Further, the 3D trace result is mapped to the entire structure and produces a full 3D image of the branch with an original MATLAB program, which will be described in further detail below (see FIG. 2D).

The dual-projection method collects emission from both lenses and has twice more photons than existing methods. The extra photon efficiency put the present method in a better position for fast volumetric imaging.

Volumetric projection imaging is faster than true 3D imaging, but it may have difficulties in resolving different layers when the 3D structure is complex. To overcome this potential problem and expand imaging ability in complex signal networks, high-resolution 3D imaging can be combined with fast volumetric projection imaging. Tissue is labeled with two fluorescent emitting markers, one for cell structure and one for function, respectively. The high-resolution 3D imaging will be performed first on structure markers. The volumetric projection imaging will be captured on both markers. Projection images of the structure marker will assist in aligning functional projection images with the high-resolution 3D images and correct any sample movement. Observed activities in function projection images will be casted to aligned 3D structure. Since in many cases activities are sparse, such approach will enable studying functions of structurally complex networks with projection imaging.

The computer program for assigning 3D structures imaged by two orthogonal projections comprises program instructions stored on a non-transitory memory of a computer and run on a processor. Before running the program, the user needs to trace, or segmenting structures seen in two 2D projections using existing imaging processing software and save the tracing or segmenting results. The program uses these results to reconstruct the 3D structure map according to the following method:

First, load in tracing or segmenting results.

Second, use a user defined list to pair the x-y projection of a trace or segment with its y-z projection.

Third, loop though all x-y plane pixel defined by the x-y trace or segment and assign a z (depth) value according to the corresponding y-z projection trace or segment result. The assignment process is carried out as:

Fourth, at a given x-y pixel on the trace or the segment, search for pixels on the y-z projection trace or segment that have the same y value. These y-z pixels provide potential z-values for the x-y pixel.

If a single match is found, the x-y pixel is given the z-value of the matched y-z pixel.

If multiple matches are found, the program compares potential z-values with previously assigned z-values of adjacent x-y pixels, and assign the x-y pixel to a z-value that is closest to adjacent pixels. This method considers that the trace or segment is continuous in the space, and the z-value difference between adjacent pixels is small.

Fifth, processes described in from the second to the fourth step are repeated on all traces or segments. This step generates traces or segments data fully mapped in 3D.

Last, the program loops through all pixels in the x-y projection image. Pixels that have observable intensity will be assigned to the z-value of its nearest trace (or segment) pixel. This approach is based on the fact that fine structures attached to a trace or segmented structures are roughly of the same depth as the main structure.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The above-described embodiments of the described subject matter can be implemented in any of numerous ways. For example, some embodiments may be implemented using hardware, software or a combination thereof. When any aspect of an embodiment is implemented at least in part in software, the software code can be executed on any suitable processor or collection of processors, whether provided in a single device or computer or distributed among multiple devices/computers.

What is claimed is:

1. A method for fast volumetric imaging of fluorescent tissue structures and activities, comprising the steps of:
   a. acquiring two orthogonal 2D projection of the sample volume, comprising:
      i. performing a projection scan with an excitation laser sweeping through the volume at a predetermined rate;
      ii. tracking the scan depth using a focus tuning device to keep the emission image in focus and generate an xy plane volume projection image at the camera; and
      iii. placing a photomultiplier tube (PMT) behind the excitation lens to collect emission passed through the excitation lens, wherein signals from the PMT form a focus scan projection at the yz plane;
   b. merging the xy and yz projections to locate positions of fluorescence emitters in 3D;
   c. tracing the structures seen in 2D projections; and
   d. reconstructing the 3D structure map by:
      i. pairing the xy projection of a trace with its yz projection;

ii. looping though all xy plane pixel defined by the xy trace and assigning a z-value according to the corresponding yz projection trace result;
iii. searching for pixels on the yz projection trace that have the same y value at a given xy pixel on the trace;
iv. assigning a xy pixel with a single match the z-value of the matched yz pixel;
v. comparing potential z-values with previously assigned z-values of adjacent xy pixels and assigning the xy pixel to a z-value that is closest to adjacent pixels; and
vi. repeating (steps i.-v.) on all traces.

2. The method according to claim 1, wherein the predetermined rate is up to 100 vps.

3. The method according to claim 1, wherein the focus tuning device is an electrically tunable lens (ETL).

4. The method according to claim 1, further comprising the step of labeling cell structure tissue of the sample volume with a first fluorescent emitting marker.

5. The method according to claim 4, further comprising the step of labeling cell function tissue of the sample volume with a second fluorescent emitting marker.

6. The method according to claim 1, further comprising the step of looping through all pixels in the xy projection image and assigning pixels that have an observable intensity to the z-value of its nearest trace pixel.

7. A system for fast volumetric imaging of fluorescent tissue structure and activities, comprising:
　a. first and second lenses each orthogonally positioned relative to the fluorescent tissue structure for acquiring two orthogonal 2D projections of the sample volume;
　b. an excitation laser for performing a projection scan by sweeping through the volume at a predetermined rate;
　c. a focus tuning device to track the scan depth and keep the emission image in focus and generate an xy plane volume projection image; and
　d. a photomultiplier tube positioned behind the first lens;
　e. means for tracing the structures seen in the 2D projections; and
　f. a computer program for assigning 3D structures imaged by the first and second lenses into a map comprising program instructions stored on a non-transitory memory of a computer and running on a processor, the computer program comprising:
　　i. means for reconstructing the 3D structure map by:
　　　a. pairing the xy projection of a trace with its yz projection;
　　　b. looping though all xy plane pixel defined by the xy trace and assigning a z-value according to the corresponding yz projection trace result;
　　　c. searching for pixels on the yz projection trace that have the same y value at a given xy pixel on the trace;
　　　d. assigning a xy pixel with a single match the z-value of the matched yz pixel;
　　　e. comparing potential z-values with previously assigned z-values of adjacent xy pixels and assigning the xy pixel to a z-value that is closest to adjacent pixels; and
　　　f. repeating (steps i.-v.) on all traces.

8. A method for fast volumetric imaging of fluorescent tissue structures and activities, comprising the steps of:
　a. acquiring two orthogonal 2D projection of the sample volume, comprising:
　　i. performing a projection scan with an excitation laser sweeping through the volume at a predetermined rate;
　　ii. tracking the scan depth using a focus tuning device to keep the emission image in focus and generate an xy plane volume projection image at the camera; and
　　iii. placing a photomultiplier tube (PMT) behind the excitation lens to collect emission passed through the excitation lens, wherein signals from the PMT form a focus scan projection at the yz plane;
　b. merging the xy and yz projections to locate positions of fluorescence emitters in 3D;
　c. segmenting the structures seen in 2D projections;
　d. reconstructing the 3D structure map by:
　　i. pairing the xy projection of a segment with its yz projection;
　　ii. looping though all xy plane pixel defined by the xy segment and assigning a z-value according to the corresponding yz projection segment result;
　　iii. searching for pixels on the y-z projection segment that have the same y-value at a given x-y pixel on the segment;
　　iv. assigning a xy pixel with a single match the z-value of the matched yz pixel;
　　v. comparing potential z-values with previously assigned z-values of adjacent xy pixels, and assigning the xy pixel to a z-value that is closest to adjacent pixels; and
　　vi. repeating (steps i.-v.) on all segments.

9. The method according to claim 8, further comprising the step of looping through all pixels in the xy projection image and assigning pixels that have an observable intensity to the z-value of its nearest segment pixel.

* * * * *